United States Patent [19]

Santi

[11] Patent Number: 4,944,752
[45] Date of Patent: Jul. 31, 1990

[54] HAIR PROSTHESIS METHOD

[75] Inventor: Claudio Santi, Savona, Italy

[73] Assignee: SALC di Pellegrino & C.S.d.f., Savona, Italy

[21] Appl. No.: 351,325

[22] Filed: May 4, 1989

Related U.S. Application Data

[63] Continuation of Ser. No. 38,396, Apr. 15, 1987, abandoned, which is a continuation-in-part of Ser. No. 838,776, Feb. 12, 1986, abandoned.

[30] Foreign Application Priority Data

Feb. 14, 1985 [IT] Italy ................................ 19513 A/85

[51] Int. Cl.$^5$ ............................................... A61F 2/10
[52] U.S. Cl. ..................................................... 623/15
[58] Field of Search ............................. 623/15; 132/73

[56] References Cited

U.S. PATENT DOCUMENTS

| 3,699,969 | 10/1972 | Allen | 623/15 |
| 3,998,230 | 12/1976 | Miller | 623/15 |
| 4,004,592 | 1/1977 | Yamada | 623/15 |
| 4,103,365 | 8/1978 | Applegate | 623/15 |
| 4,126,124 | 11/1978 | Miller | 623/15 |
| 4,144,876 | 3/1979 | De Leo | 623/15 |
| 4,552,160 | 11/1985 | Griggs | 132/73 |
| 4,588,408 | 5/1986 | Yamada | 623/15 |
| 4,687,827 | 8/1987 | Russo | 132/73 |

Primary Examiner—David J. Isabella
Attorney, Agent, or Firm—Peter K. Kontler

[57] ABSTRACT

A method for prosthetic implantation which is effective to provide for a partial or total prosthetic implant of hairs, and which utilizes at least one natural hair which is terminated with a pseudo-bulb or loop intended for insertion into the subcutaneous region of the scalp, wherein the looped pseudo-bulb exhibits elasto-rigid properties.

12 Claims, 2 Drawing Sheets

HAIR PROSTHESIS METHOD

CROSS-REFERENCE TO RELATED CASE

This is a continuation of co-pending application Ser. No. 07/038,396 filed on Apr. 15, 1987, which is a Continuation-in-part application of Ser. No. 838,776, filed Feb. 12, 1986, now abandoned.

BACKGROUND OF THE INVENTION

This invention relates to a hair prosthesis useful to form a partial or total prosthetic implant of hairs.

Already known are a number of methods for eliminating partial or total baldness, but such prior methods have the disadvantage of being either very expensive, or of having an unnatural look, or of being unsuccessful over time.

It is known to implant artificial hairs and also natural hairs wherein the anchorage is provided by knots formed on the hairs. Such implants are not reversible i.e., the hairs cannot be removed without a surgical intervention, since the knots cannot be undone. Artificial hairs formed by synthetic fibers are much more stiff than the natural ones, causing a greater trauma to the skin.

Also known is, e.g. from Italian Patent Application No. 68405 A/82, a prosthesis for hair transfer which comprises a length of an inert material yarn carrying a lock or tuft of hairs tied to both ends thereof. By surgical intervention, such locks are implanted in the scalp such that the synthetic yarn becomes embedded in the scalp to serve as an anchor means and the two end locks of hairs extend from the scalp surface. That prosthesis type is not only complicated as relates to its surgical aspect, but fails to provide a hair prosthesis with a natural appearance.

In prior art arrangements using natural (human) hairs, they are usually coated with reinforcing and adhesive substances to make them stronger and these substances may have toxic effects and cannot be removed. As an alternative, a number of hairs have been used for each tuft to get a greater strength, but the size of the implanted portion becomes greater and can easily cause irritation.

Although it is known to implant individual hairs in the scalp which are formed from a synthetic material, in this case, intoxication symptoms may appear which result in tissue inflammation due to the dyestuffs present in a prosthesis from synthetic material hairs. Such minute amounts of dyestuffs are unavoidably released over time and are a cause of irritation.

SUMMARY OF THE INVENTION

It is, accordingly, an object of this invention to provide a novel method for partial or total prosthetic implantation of hairs, which exhibits none of the drawbacks exhibited by prior approaches, and specifically affords a fast rate of implantation of the prosthesis in the scalp, adaptability to any requirements by the patient, and above all, utilizes a prosthesis which is formed from natural, non-dyed and non-toxic hairs.

The above object is achieved in that several natural hairs are used having, at their ends corresponding to the hair roots, a looped pseudo-bulb termination intended for introduction into the subcutaneous region of the scalp.

The looped pseudo-bulb is formed, most advantageously, by entwining together the terminating ends of the hairs.

Also advantageous is that the looped pseudo-bulb is secured by means of an inert adhesive so as to exhibit elasto-rigid properties.

Expediently, the adhesive types for use herewith would be selected from those commercially available for surgical applications or prosthesis making, so long as their non-toxic and inert character has been well proven over time. For example commercial adhesives may be used which are known under the tradenames of "Kemicyak" or "Histoacryl".

Further features and advantageous embodiments of the invention are set forth in the description that follows and in the drawings.

DESCRIPTION OF THE PREFERRED EMBODIMENTS

Figure 1:
FIG. 1 shows a lock or tuft of four hairs without the terminating bulb.

As may be seen in FIG. 1, a number of hairs, which may vary from one or two hairs up to ten, are laid parallel to one another. Natural hairs may be used without any chemical treatment, with the exception of the adhesive, described in more detail below. The natural hairs 1 are laid such that their keratinous scales agree in lay with the natural hairs left to the patient. Of course, the hair color and the number of the hairs forming a lock will be subject to variations where, for example, a more or less thick hair is aimed at, and on the implantation zone, for example, whether the forehead, temples, or areas specially in view.

To make the implant appear even more realistic and natural, it would be possible, for example, to use a lock of different color and thickness hairs, also including scattered grey hairs. This expedient is apt to make the end result considerably more natural-looking and resembling real growth.

Figure 2:
FIG. 2 shows the lock of FIG. 1 during the making of a terminating bulb of loop-like configuration.

As shown in FIG. 2, the hairs 1 are entwined at their ends, which would correspond to the bulb ends of natural hairs, into a pseudo-bulb which is configured, however, as a small loop or ring 2. This loop or ring will have, advantageously, a diameter in the range of about 0.5 to about 2 mm. The actual size of loop 2 forming the pseudo-bulb is dictated essentially by the thickness of depth dimension of the skin which is to receive the implant. Substantially smaller loops would not allow for a sufficient grip whereas substantially larger ones could produce a too traumatic implantation. As previously mentioned, hairs 1 are laid in agreement with the natural lay of the keratinous scales.

Figure 3:
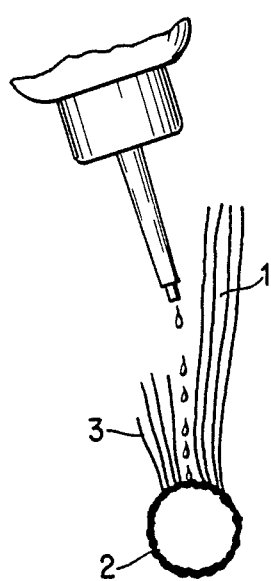
FIG. 3 illustrates the application of an inert cement for setting the intertwining in place.

In order to firmly secure the termination formed of entwined hair loop 2, and simultaneously provide a small terminating loop with elasto-rigid properties, as may be seen in FIG. 3, the entwining is applied with one or more drops of an inert adhesive, e.g. an adhesive selected from those usually employed in surgery and prosthesis making. Such adhesives are non-toxic and of the type which, under normal conditions, dissolve slowly enough to allow for the complete healing and the gripping of the hair by the healing tissue. In suppurative environment the adhesive dissolves very rapidly. Suitable adhesives include inorganic cyano-acrylates such as iso-butyl-cyano-acrylate and methyl-2-cyano-acrylate, adhesives available under the trade names of "Histoacryl" or "Kemicyak", both commercially available. Suitable organic adhesives include those based on human fibrin such as "Tissucol", commercially available. On applying the adhesive in drops, as shown in FIG. 3, the adhesive will wet by capillary effect loop 2 throughout which forms the psuedo-bulb. After the adhesive has set, a terminating loop 2 is obtained which has elasto-rigid properties. This feature of loop 2 is highly important to insertion and securement of the hair prosthesis 1, 2 into the patient's skin. It should be pointed out, however, that loop 2 forming the pseudo-bulb is the only portion provided with elasto-rigid properties, from loop 2 lock-forming hairs 1 extend in a natural and quite unrestricted way.

Advantageously, the lock would comprise 3-10 hairs gathered to form a single pseudo-bulb 2.

Figure 4:
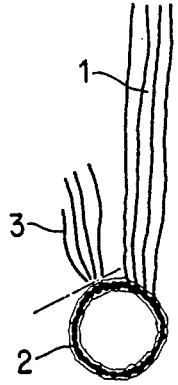
FIG. 4 illustrates diagrammatically the final cutting of the hairs extending from the elasto-rigid pseudo-bulb or loop.

After the adhesive has set, as may be seen in FIG. 4, the short ends 3 of the hairs 1 are cut off to provide a pseudo-bulb loop 2 which is closed and smooth, that is without protrusions.

Figure 5:
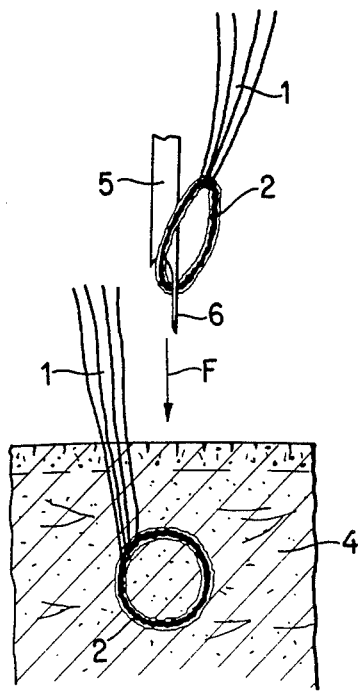
FIG. 5 illustrates diagrammatically the step of inserting the pseudo-bulb of the hair lock into the scalp with the assistance of a forked end needle.
Figure 6:
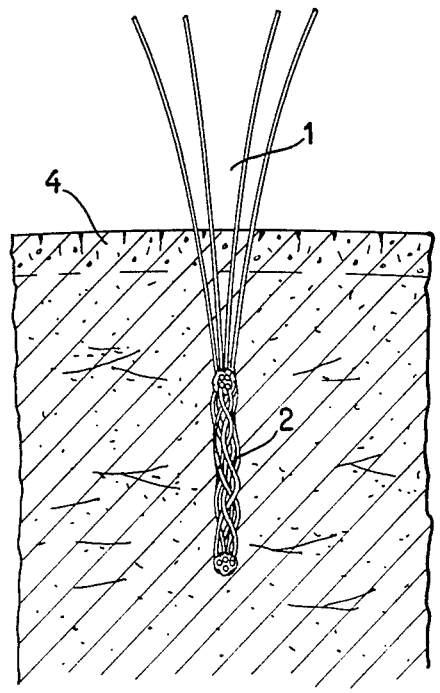
FIG. 6 is a larger-scale cross-sectional view of the hair lock in its implanted state.
Figure 7A:
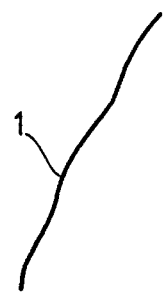
FIGS. 7a-7g illustrates diagrammatically the method of this invention wherein one hair is used to form the prosthetic implant.
Figure 7B:
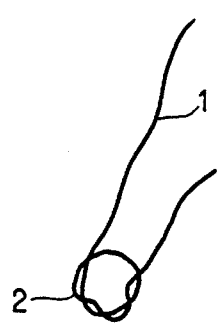
Figure 7C:
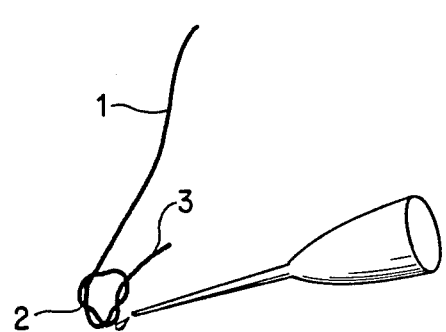
Figure 7D:
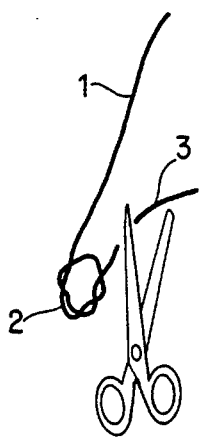
Figure 7E:
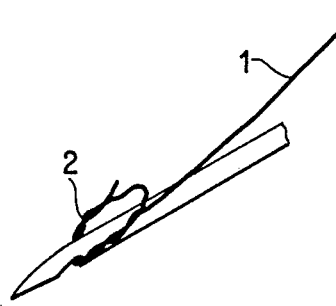
Figure 7F:
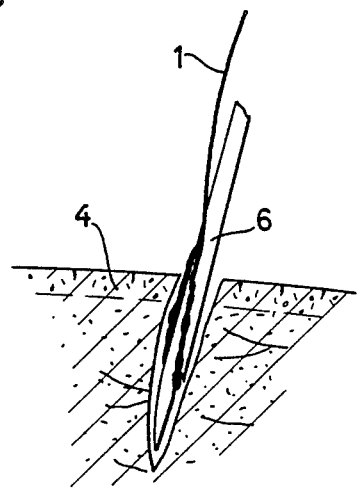
Figure 7G:
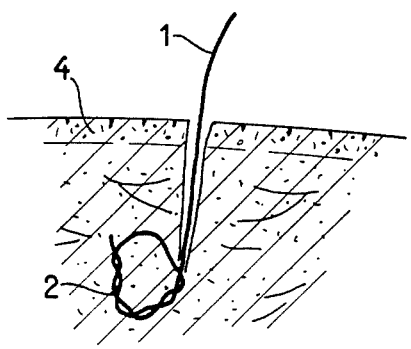

As shown in FIG. 5, the lock of hairs 1, in the course of a simple surgical intervention, will be sunk with its elasto-rigid pseudo-bulb loop 2 in the thickness of the scalp 4 to a depth of about 5 mm. Of course, the depth of implantation of the looped pseudo-bulb 2 will be selected by the operator and vary with the size of the loop 2 forming the pseudo-bulb as well as with the thickness of the scalp. To implant a lock of hairs 1 into the scalp 4, the looped pseudo-bulb 2 is mounted to the end of a needle 5 having a forked tip 6 for receiving, as shown, the pseudo-bulb loop 2.

To attain a partial or total prosthetic thickening, plural hair locks 1 would be implanted at convenient distance apart, in accordance with aesthetic consideration.

It should be further emphasized that locks having a varying number of hairs may be used. The possibility of using a multiple hair lock affords in fact the possibility of implanting more hairs for a given number of surgical interventions. This represents an important advantage over implanting methods on a single hair basis.

Traumatic effects on the tissue, for a given number of hairs implanted, are thus attenuated, which greatly reduces the risks of subsequent infection.

As already mentioned, it is advantageous to use a needle 5 having a forked tip 6 to which the loop of the pseudo-bulb 2 of the lock of hairs 1 is engaqed. By moving the needle in the direction of the arrow f, the elasto-rigid pseudo-bulb 2 is inserted into the scalp.

Advantageously, the diameter of the needle 5 is selected to be smaller than the diameter of the loop 2 forming the pseüdo-bulb, e.g. the needle 5 may have a diameter of 0.3 to 0.6 mm. Due to that differential—the loop of the pseudo-bulb 2 being much larger, e.g. having a diameter of 0.5 to 2 mm—and the elastic deformability of the loop 2 during insertion of the pseudo-bulb 2 into the skin 4, the loop is squeezed elastically, and once it has been inserted into the skin 4, will tend by natural elasticity to return to its original diameter, thus providing a firm anchorage and causing the hairs 1 in the lock to be firmly caught in the smaller channel that closes on withdrawing the needle 5. This already provides a degree of securement of the prosthesis owing to the mechanical clamping action of the walls of the channel on the hairs 1, which allow combing or washing of the hairs even before complete healing takes place. Since the hair results in being firmly implanted and not subjected to movement, the healing is faster.

The risk of infection is greatly reduced in using the method of this invention and the skin begins to heal at once. Complete healing usually takes place in about twenty days.

It results that the looped pseudo-bulb 2 having a much larger diameter than the insertion channel, on expanding immediately after insertion by virtue of the elasto-rigid properties of the loop 2, thanks to the inert adhesive used, is prevented from coming out easily through the insertion channel which is narrower. Thus, directly on implanting it, the lock of hairs 1 is held firmly in the skin by mechanical action.

Furthermore, the looped pseudo-bulb 2 is then through-penetrated by healing tissue from the skin owing to its being held open by its elasto-rigid features, and accordingly, the tissue growth through the loop 2 will further anchor, on healing, the lock of hairs 1 and its pseudo-bulb 2 firmly in the subcutaneous region of the scalp.

Single hairs 1 can also be implanted using this invention, the method for a single hair providing for an interwinding of at least two turns, the application of the adhesive to fix the size of the loop 2, the cutting of the short end 3 and the implantation with a needle having a groove near the tip 6, as illustrated in FIGS. 7a-7g.

The needle 6 engages the loop 2 at a point where the hair is double, i.e. at a point of very high resistance, even in the case of a single hair. By gently pulling the free end of the hair, the loop 2 engages the needle pocket 6 always at the same position of high resistance. Since the loop 2 is slightly larger than the needle 6 it tends to spread immediately after the implantation.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

I claim:

1. A method of permanently implanting human hair in human skin comprising the steps of forming one end portion of at least one human hair into a knotted elasto-rigid loop which is devoid of outwardly extending protrusions; attaching said loop to the tip of an implanting tool having a diameter less than that of said loop; introducing said tool and said loop into the subcutaneous region of a selected portion of the human skin at a selected entry point so that said tool provides a path for introduction of said loop into the skin and introduces said loop into the subcutaneous region of the skin; and extracting said tool by way of the selected entry point.

2. The method of claim 1 which further comprises imparting elasto-rigid properties to said loop by application of an inert adhesive.

3. The method of claim 2 wherein said adhesive comprises a cyano-acrylate composition.

4. The method of claim 1 wherein said loop is formed of a plurality of hairs which are gathered into a tuft wherein the one end portion of each hair of said plurality of hairs is adjacent the one end portion of each other hair.

5. The method of claim 4 wherein said loop is formed by entwining the one end portion of each of said plurality of hairs with the one end portion of at least one other hair.

6. The method of claim 4 wherein said tuft comprises 3 to 10 hairs.

7. The method of claim 4 wherein said hairs which are gathered into said tuft have varying color and thickness.

8. The method of claim 1 wherein said loop has a diameter of 0.5 mm to 2.0 mm.

9. The method claim 1 wherein said tool has a forked tip.

10. The method of claim 1 wherein said tool has a diameter of 0.3 mm to 0.6 mm.

11. The method of claim 1, wherein said converting step comprises bending the one end portion of the at least one hair into the shape of a ring with an outwardly projecting free end, and removing the free end.

12. The method of claim 1, wherein said converting step comprises entwining the one end portion into a stable ring.

* * * * *

UNITED STATES PATENT AND TRADEMARK OFFICE
CERTIFICATE OF CORRECTION

PATENT NO. : 4,944,752
DATED : July 31, 1990
INVENTOR(S) : Claudio SANTI

It is certified that error appears in the above-identified patent and that said Letters Patent are hereby corrected as shown below:

On the title page: Item (63) Related U.S. Application Data - "838,776" should read --828,776--.
Col. 1, line 7, "838,776" should read --828,776-.
Col. 2, line 1, "advantaqe-" should read --advantage- --.
Col. 3, line 62, "engaqed" should read --engaged--.

Signed and Sealed this

Tenth Day of March, 1992

Attest:

HARRY F. MANBECK, JR.

Attesting Officer

Commissioner of Patents and Trademarks